United States Patent
Sutter

(10) Patent No.: US 11,207,038 B2
(45) Date of Patent: Dec. 28, 2021

(54) METHOD FOR COLLIMATOR ELEMENT ADJUSTMENT OF AN X-RAY SYSTEM

(71) Applicant: Siemens Healthcare GmbH, Erlangen (DE)

(72) Inventor: Sven-Martin Sutter, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 74 days.

(21) Appl. No.: 16/819,559

(22) Filed: Mar. 16, 2020

(65) Prior Publication Data

US 2020/0312478 A1   Oct. 1, 2020

(30) Foreign Application Priority Data

Mar. 29, 2019   (DE) .......................... 102019204508.1

(51) Int. Cl.
| | |
|---|---|
| *A61B 6/06* | (2006.01) |
| *A61B 6/08* | (2006.01) |
| *G21K 1/02* | (2006.01) |
| *A61B 6/00* | (2006.01) |

(52) U.S. Cl.
CPC .................. *A61B 6/08* (2013.01); *A61B 6/06* (2013.01); *A61B 6/469* (2013.01); *A61B 6/545* (2013.01); *G21K 1/025* (2013.01)

(58) Field of Classification Search
None
See application file for complete search history.

(56) References Cited

U.S. PATENT DOCUMENTS

| | | | | |
|---|---|---|---|---|
| 6,502,984 | B2 * | 1/2003 | Ogura ...................... | A61B 6/06 378/206 |
| 6,731,718 | B2 * | 5/2004 | Ogura ...................... | A61B 6/06 250/206 |
| 7,581,884 | B1 * | 9/2009 | Barnes ...................... | A61B 6/06 378/164 |
| 7,798,710 | B1 * | 9/2010 | Barnes ...................... | A61B 6/06 378/206 |
| 10,813,617 | B2 * | 10/2020 | Inoue ........................ | A61B 6/06 |
| 2001/0012330 | A1 * | 8/2001 | Ogura .................... | A61B 6/588 378/95 |

(Continued)

FOREIGN PATENT DOCUMENTS

| | | |
|---|---|---|
| CN | 108937998 A * | 12/2018 |
| DE | 102012202498 A1 | 8/2013 |

(Continued)

*Primary Examiner* — Thomas R Artman
(74) *Attorney, Agent, or Firm* — Harness, Dickey & Pierce, P.L.C.

(57) ABSTRACT

A method is for collimator element adjustment of an x-ray system with a central x-ray axis and an optical axis of an optical imaging device differing therefrom. In an embodiment, the method includes displaying a first recorded optical image of the examination object; marking a target region as a region to be shown in the displayed first recorded optical image; determination of at least one first collimator element position value based on the marked target region in the first recorded optical image; and adjustment of the collimator element position with the at least one first collimator element position value determined.

30 Claims, 4 Drawing Sheets

(56) References Cited

U.S. PATENT DOCUMENTS

| | | | | |
|---|---|---|---|---|
| 2003/0095636 | A1* | 5/2003 | Ogura | A61B 6/544 |
| | | | | 378/205 |
| 2018/0116623 | A1* | 5/2018 | Inoue | H05G 1/00 |
| 2019/0290236 | A1* | 9/2019 | Oepping | A61B 6/4405 |
| 2020/0312478 | A1* | 10/2020 | Sutter | G21K 1/025 |
| 2021/0093284 | A1* | 4/2021 | Sutter | A61B 6/5258 |

FOREIGN PATENT DOCUMENTS

| | | | | |
|---|---|---|---|---|
| DE | 102013215516 A1 | * | 2/2015 | A61B 6/0407 |
| KR | 101689082 B1 | * | 12/2016 | |

* cited by examiner

METHOD FOR COLLIMATOR ELEMENT ADJUSTMENT OF AN X-RAY SYSTEM

PRIORITY STATEMENT

The present application hereby claims priority under 35 U.S.C. § 119 to German patent application number DE 102019204508.1 filed Mar. 29, 2019, the entire contents of which are hereby incorporated herein by reference.

FIELD

Embodiments of the invention generally relate to a method for collimator element adjustment of an x-ray system, wherein the central x-ray axis and an optical axis of an optical imaging device are different, and also to an x-ray system for this purpose.

BACKGROUND

Known x-ray systems comprise an x-ray source, an x-ray detector and a collimator element system or a collimator system. The collimator element system can include an arrangement of different collimator elements and filters and is usually arranged at least partly on the x-ray protection housing of the x-ray source. The collimator element system can lead to the reduction of the scatter radiation and thus to enhanced contrast of the recorded image data and can moreover reduce the radiation load for the patient. Before the x-ray imaging is carried out the collimator element system must be adjusted. In particular the collimator elements the must be positioned for recording the respective image.

A method for positioning a collimator system of an x-ray device is known from publication DE 10 2012 202 498 A1. A target region is marked in a displayed preview recording as a region to be shown. Collimator position values are computed automatically on the basis of the marking data, which are used for automatic positioning of the collimators. However this method generally leads to an unnecessary radiation load on the patient.

SUMMARY

The inventor has discovered the following problem that the central ray of the x-ray system and the optical axis of a camera system are not identical as a rule, and therefore the optical image and the light field of the collimator element system will be shown at different positions or different geometries. If in an x-ray image recording the collimator element position is to be marked after recording of an optical image via a target region on the optical image and the mechanical collimator element adjusted to this position, then in accordance with the present invention it is necessary to establish the collimator element position while taking into account the distance between the central ray and the optical axis. Moreover the distance between x-ray source and object is not able to be derived from a two-dimensional image, so that a unique computation of the collimator element position under the conditions given above is not possible.

Embodiments specify a method for collimator element adjustment, a collimator element adjustment unit, an x-ray system, a computer program product and a computer-readable medium, which make it possible to establish the collimator element position based on a recorded optical image.

Embodiments of the invention are directed to a method for collimator element adjustment, a collimator element adjustment unit, an x-ray system, a computer program product and a computer-readable medium.

At least one embodiment of the invention relates to a method for collimator element adjustment of an x-ray system with a central x-ray axis and an optical axis of an optical imaging device differing therefrom. The central x-ray axis of the x-ray source and the optical axis of the optical imaging device are directed on the examination object. In particular the optical imaging device can be a 2D or 3D camera. The optical imaging device can record an optical image. The optical axis is different from the central x-ray axis. In particular the optical axis and the central x-ray axis are not congruent. For example the optical axis and the central x-ray axis are shifted laterally in relation to one another and/or are tilted. For example the optical axis and the central x-ray axis run in parallel or at an angle to one another.

In at least one embodiment, the inventive method comprises, in particular in the following order:

Display of a first recorded optical image of the examination object,

Marking of a target region as region to be shown in the first optical image displayed, First determination of at least one first collimator element position value based on the marked target region in the first recorded optical image, and First adjustment of the first collimator element position with the at least one first collimator element position value determined.

At least one embodiment of the invention further relates to a collimator element adjustment unit, comprising:

A user interface, at which a first recorded optical image is displayed, in which at least one region to be shown as the target region is able to be marked, A determination unit, which is intended for automatic determination of collimator element position values, based on marking data for the target region entered via the user interface and based on geometrical parameters of the collimator element system, A computer-controlled positioning mechanism, which adjusts the collimator element system with the collimator element position values determined by the determination unit.

At least one embodiment of the invention further relates to an x-ray system having an inventive collimator element adjustment unit of at least one embodiment. Preferably the imaging device is thus based on x-rays. This can involve a usual x-ray device of a computed tomography system.

At least one embodiment of the invention further relates to a computer program product with a computer program, which is able to be loaded directly into a memory device or a control device of an x-ray system, with program sections for carrying out all steps of at least one embodiment of an inventive method when the computer program is executed in the control device of the x-ray system.

At least one embodiment of the invention further relates to a product, in particular a computer program product, which can be loaded into an internal memory of a digital computer and comprises software routines with which the steps of at least one embodiment of the methods described above are carried out, when the software routines are loaded onto the digital computer and/or executed. In such cases the software routines can be embodied as a computer program. The computer program can be stored on a storage medium (comprising an exchangeable storage medium, such as memory cards for example). The determination unit can serve to carry out the methods described above.

At least one embodiment of the invention further relates to a computer-readable medium, on which program sections able to be read in and executed by a processor unit are stored in order to carry out all steps of at least one embodiment of an inventive method when the program sections are executed by the collimator element adjustment unit.

At least one embodiment of the invention further relates to a method for collimator element adjustment of an x-ray system with a central x-ray axis and an optical axis of an optical imaging device differing therefrom, the method comprising:

displaying a first recorded optical image of an examination object;

marking a target region as a region to be shown in the first recorded optical image displayed;

determining at least one first collimator element position value based on the target region marked in the first recorded optical image; and adjusting a position of collimator element position based upon the at least one first collimator element position value determined.

At least one embodiment of the invention further relates to a collimator element adjustment unit for collimator element adjustment of a collimator element system, comprising:

a user interface, at which a first recorded optical image is shown, at least one region of the first recorded optical image being markable as a target region to be shown in the optical image;

a determination unit, to automatically determine collimator element position values, based on marking data for the target region entered via the user interface and based on geometrical parameters of the collimator element; and a computer-controlled positioning mechanism, to adjust the collimator element system with the collimator element position values determined by the determination unit.

At least one embodiment of the invention further relates to a non-transitory computer program product storing a computer program, directly loadable into a memory device of a control device of an x-ray system, including program sections for carrying out the method of an embodiment when the computer program is executed in the control device of the x-ray system.

At least one embodiment of the invention further relates to a non-transitory computer-readable medium, storing program sections readable and executable by a processing unit, to carry out the method of an embodiment when the program sections are executed by the processing unit.

BRIEF DESCRIPTION OF THE DRAWINGS

Explained in greater detail below on the basis of drawings are example embodiments of the invention. In the figures.

DETAILED DESCRIPTION OF THE EXAMPLE EMBODIMENTS

Figure 1:
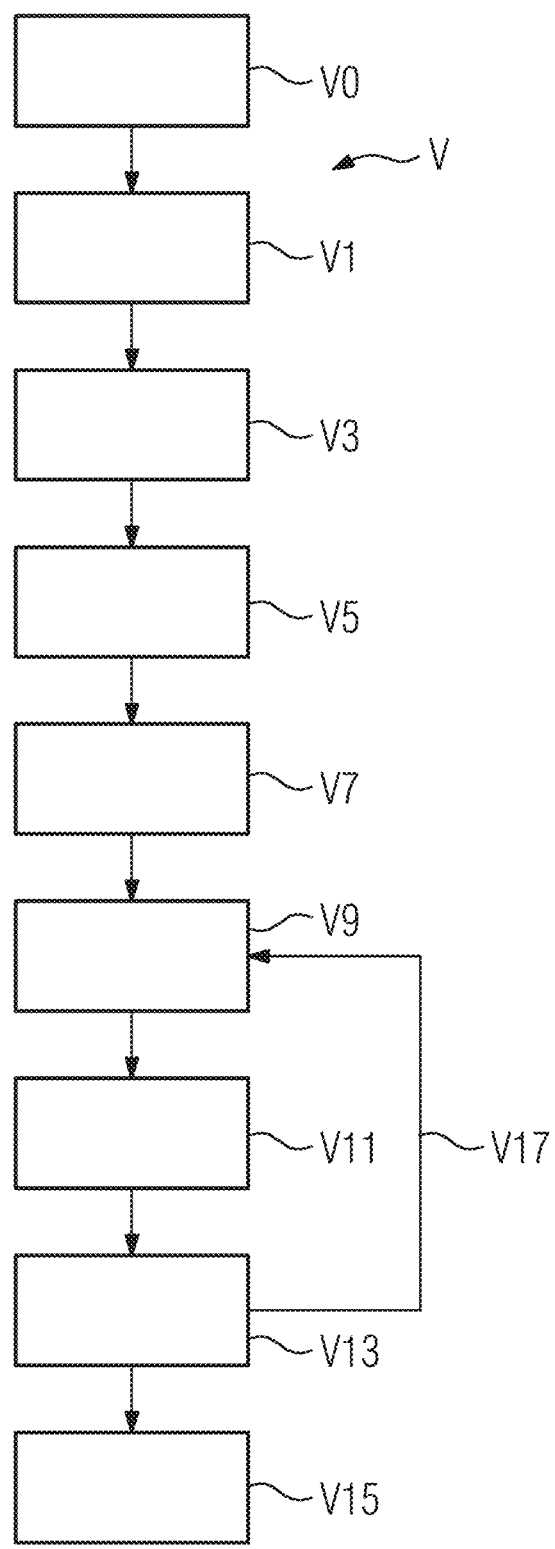
FIG. 1 shows a schematic diagram of an embodiment of the inventive method.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for collimator element adjustment of an x-ray system with a central x-ray axis and an optical axis of an optical imaging device differing therefrom. The central x-ray axis of the x-ray source and the optical axis of the optical imaging device are directed on the examination object. In particular the optical imaging device can be a 2D or 3D camera. The optical imaging device can record an optical image. The optical axis is different from the central x-ray axis. In particular the optical axis and the central x-ray axis are not congruent. For example the optical axis and the central x-ray axis are shifted laterally in relation to one another and/or are tilted. For example the optical axis and the central x-ray axis run in parallel or at an angle to one another.

In at least one embodiment, the inventive method comprises, in particular in the following order:

Display of a first recorded optical image of the examination object,

Marking of a target region as region to be shown in the first optical image displayed, First determination of at least one first collimator element position value based on the marked target region in the first recorded optical image, and First adjustment of the first collimator element position with the at least one first collimator element position value determined.

First of all an, in particular first, optical image of the examination object can be recorded via an optical imaging device. The first recorded optical image of the examination object is displayed, on a display device or user interface for example, in particular a screen, which are assigned to the x-ray system.

The target region is marked as the region to be shown in the first optical image displayed. I.e. after recording of the first optical image the user can draw in or mark the target region, for example ROI or VOI. The target region is marked manually in the displayed preview image recording. The target region is thus an ROI region (region of interest) or VOI region (volume of interest), which is to be shown with the collimator element system. After acquisition of the marking data the system can establish the first collimator element position value automatically, which will then be passed on to a computer-assisted or computer-controlled positioning mechanism, in order to adjust the collimator element system with the determined first collimator element position value. This is preferably done automatically and does not require any further inputs or movements of the hand by the doctor or medical personnel.

In the first determination step, at least one first collimator element position value is determined in at least one embodiment, based on the marked target region in the first recorded optical image. In this case the essentially known arrangement of the optical axis in relation to the central x-ray axis and/or the extent or size of the target region can be used. The collimator element position value can be a central position of the light field or a light field size for example.

Since the, for example mechanically predetermined, deviation of the optical axis in relation to the central x-ray axis can essentially be known, the, in particular desired, central position of the first collimator element position or of the first light field, i.e. an indication of the collimator element on the surface of the examination object, can be estimated. The center of light field can be positioned at the desired central position. The extent or the size of the light field can be estimated from the extent or the size of the target region.

In particular when a 2D camera is used as the optical imaging device the distance between the surface of the examination object and the x-ray source is essentially unknown, since initially depth information to determine the distance is missing. When a 3D camera or in general a system for depth measurement is used the distance can be estimated or determined via the first recorded optical image. In the case of a 3D camera the first collimator element position can advantageously be determined more precisely for the target region than if a 2D camera is used. If necessary the first collimator element position can satisfy the requirements in respect of accuracy in the match with the target region, so that further steps for determination of the second collimator element position can be avoided. Advantageously the collimator element can be adjusted more precisely and more quickly.

In at least one embodiment, in the first adjustment step, the first collimator element position is adjusted with the at least one first collimator element position value determined.

One embodiment of the invention further comprises, in particular in the following order:

Recording of a second recorded optical image at a first light field shown with the at least one collimator element position value shown, Second establishment of at least one second collimator element position value based on the comparison of the first light field and of the target region in the second recorded optical image, and Second adjustment of the second collimator element position with the at least one second collimator element position value determined.

These steps are in particular intended for the use of a 2D camera or for checking or correction of the first collimator element position, even if a 3D camera or the like is used. In the recording step a second optical image recording can be made with a first light field shown with the adjusted at least one collimator element position value. At least one second optical image recording or a second optical image can be measured with a light field switched on or shown. Further optical images can be measured with a light field switched on or shown, so that the method can be designed iteratively.

To adjust an, in particular second, light field or the second collimator element position the method can begin for example with a modified, for example smaller, size of the light field. The size of the light field can then be modified continuously, in order to approach the estimated size of the light field. The inventive method can comprise a dynamic adaptation of the light field to the target region previously marked in the recorded optical image. In the acquired or recorded optical image or a plurality thereof the size of the light field is analyzed by image processing and compared to the size of the previously marked target region.

In the second establishment step at least one second collimator element position value can be determined based on the comparison of the first light field and of the target region in the second recorded optical image. For example a second central position of a second light field and/or a second light field size can be determined. When collimator elements, in particular collimator elements only able to be moved symmetrically, are used, the central position can be optimized by distance comparisons, for example of the edges of the target region with edges of the light field displayed.

In the second adjustment step the second collimator element position, in particular of the second light field, can be adjusted with the at least one second collimator element position value determined.

Since the x-ray source must be shifted to align the central x-ray to the central position of the target region under some circumstances, this movement can be taken into account by the first and/or second adjustment step. The method can be embodied in particular as an adjustment algorithm.

A collimator element system is the arrangement of least one collimator element, which is arranged in the ray path between x-ray source and x-ray detector. Lead or tungsten as a component of the collimator element material is used as a rule for x-ray sources. An x-ray system can contain collimator elements, collimators and filters as a rule, which are used for shielding from scatter radiation, for determination of the region to be examined (region/volume of interest) and for absorption of low-energy components of the x-ray spectrum. The units mentioned here can be a component of the collimator element system.

In accordance with one embodiment of the invention and depending on the type of x-ray system and of imaging, for example computed tomography, radiography, angiography, mammography or similar, the collimator element can be provided in different forms or types, e.g. as a cross collimator, multileaf, slot or leaf collimator, aperture collimator and/or iris collimator. Moreover it is possible to provide the collimator element as a fixed or adjustable collimator element. A collimator element can in particular comprise two collimator element units, which are able to be moved towards each other. Moreover the collimator element system can also comprise filters, e.g. form filters or a number of filters, which can be possibly combined and/or exchanged separately in a filter insert in the collimator element system. Likewise it is possible to push a filter into the collimator element, in order to be able to filter out a specific spectrum from the original radiation.

In a typical arrangement of an x-ray system a radiation filter and usually subsequently a collimator element are provided in the radiation path in front of the object. A scattered radiation can be provided behind the examination object and in front of an x-ray detector. Likewise it is possible also to provide a collimator element close to the object in front of the object. In the simplest form of embodiment the collimator element system comprises just one collimator element. More complex forms of embodiment provide for a number of collimator elements and/or filters, which can be inserted as movable elements into the ray path as required.

In a usual form of embodiment the x-ray source is integrated into a radiation protection housing. Furthermore a multileaf collimator element (usually made of lead) is fastened to the radiation protection housing, which serves to restrict the radiation on the patient side. Moreover a light-beam localizer is integrated into the radiation protection housing. The light-beam localizer can thus serve as a user interface, on which x-ray radiation field restricted via the collimator element system is shown optically as the light field on the surface of the patient. The invention can basically be applied to all different types of collimator element systems—and thus to collimator elements on the x-ray source side and/or on the detector side. Preferably however the invention relates to collimator elements that are arranged and/or are movable and/or comprise different types of collimator elements and/or filters.

In the preferred form of embodiment the recorded optical image is displayed on a screen of the control computer. The user can then mark the target region to be shown in the recorded optical image displayed with different marking methods. The collimator element position values can be determined from the acquired marking data, in order to be able to position the corresponding collimator elements or filters automatically, so that the target region is shown. Depending on application however it can also be necessary to define a number of target regions or one target region, which can comprise separate or divided region sections. Preferably the region sections are located in one image. For example this can involve smaller, delimited pathological structures of an organ, which are shown on the displayed recorded optical image. The region to be shown or the light field is then automatically selected so that the target region covers the marked region sections as comprehensively as possible.

The collimator element position value is computed automatically via a processor or via the establishment unit and passed to the motor for control of the positioning mechanism. Thus the individual modules of the imaging device are addressed and controlled differently. In particular the establishment unit is embodied in the execution sequence of a technical (imaging) device, in particular an x-ray system. In the form of embodiment of the invention in which the positioning and adjustment method is implemented by software, the data processing program used to solve the problem is determined by the optical-physical circumstances outside the program, for example selection and position of the collimator element and the projection laws.

A collimator element position value in particular involves a value that is sufficient for positioning a component or a number of components of the collimator element systems (filters, collimator elements etc.). A collimator element position value can be provided for each component or units of components. The collimator element position value thus comprises a position specification for at least one collimator element. Moreover the collimator element position values can also comprise configuration data that relates to the form and/or type of the respective collimator element (but also e.g. to material of the collimator element, filters to be inserted, inserts, size etc.). If the collimator element system includes a number of different collimator elements, then the collimator element position values comprise all necessary collimator element-specific specifications for selecting and positioning the respective collimator elements. The collimator element position values thus also relate in an advantageous development of the invention to a combination of the collimator elements employed, for example a first collimator in position X, second collimator in position Y, third collimator with filter insert A etc.

The geometrical parameters of the collimator element systems are known or are read in. The geometrical parameters are provided to a determination unit, which is used for computation of the collimator element position values. The determination unit then passes on the result that it has determined, namely the collimator element position values, to the computer-controlled positioning mechanism, in order to configure the collimator element system automatically, for example by selecting the collimator elements to be employed and to be positioned. The geometrical parameters can involve an enlargement factor, which is computed from the ratio between x-ray focus-x-ray detector distance and x-ray focus-examination object distance. The position of the focal point or x-ray focus of the x-ray tubes as geometrical parameters and the projection laws can be provided. The projection laws are held so to speak as formulae in the determination unit, optionally variable, in order to the apply these to the concrete values.

Advantageously a simple adjustment of the collimator element position at the operating console, at the display unit, the screen, or at the user interface can be made possible. Advantageously a simpler and timesaving option for optimizing the collimator element position can be achieved. Advantageously an iterative collimator element adjustment with the aid of an, in particular low-cost, 2D camera can be achieved. An algorithm for image analysis of the first and the second recorded optical image can advantageously be used. Advantageously the workflow at the customer or user can be optimized. Advantageously an image analysis can be used for determination of the light field displayed on the recorded optical image. Advantageously a continuous adaptation of the target coordinates or of the collimator element position value can be carried out during the recording of the optical images. Advantageously the target position of the collimator element can be computed with the second, in particular final, collimator element position value from a number of measurement points or a number of recorded optical images.

In accordance with one embodiment of the invention, the collimator element position value is a central position of the light field or a light field size. The collimator element position value can relate to the size on the surface of the light field. The collimator element position value can comprise a position of the, in particular respective, collimator element. The central position of the light field can for example refer to the center of gravity of the surface of the light field. The central position can designate a point on the axis, which runs along the boundary of for example two opposite collimator elements in the closed state. The point can be embodied in particular at the central point of the boundary. The central position can in particular comprise a position coordinate of the point at which the central x-ray strikes within the surface able to be shown. Advantageously an especially homogeneous x-ray radiation field can be used.

In accordance with one embodiment of the invention, the first optical image and/or the second optical image are recorded in relation to the optical axis. The respective optical image is recorded by the imaging device, wherein the imaging device records a view along the optical axis of the imaging device. The angle of view of the recorded optical image is altered in relation the x-ray source, for example by offset and/or skewed installation, compared to the angle of view of the x-ray source. Advantageously x-ray source and imaging device can be permanently embodied alongside one another, so that a permanently defined relationship is embodied between the central x-ray axis and the optical axis.

In accordance with one embodiment of the invention, the first light field is shown in the display in relation to the central x-ray axis. The first (and second) light field are shown in the display via the collimator elements. The light source is located close to the x-ray source, wherein the light can be introduced via mirrors into the ray path of the x-ray source, for example as a light-beam localizer. Advantageously by way of the light field the x-ray radiation field can be indicated on the surface of the patient or shown in the display. Advantageously the recording region for the x-ray recording can be visualized on the surface of the patient and thereby checked or defined.

In accordance with one embodiment of the invention, the steps of recording, of second determination and of the second adjustment are repeated, so that the second collimator element position value is determined iteratively. The second recorded optical image in particular shows a new first light field during the repetition loop based on the second collimator element position with the at least second collimator element position value determined. The new first light field can also be referred to as the second light field. The newly defined second collimator element position with the new second collimator element position value as a rule shows an improved match between the light field shown and the target region. The second collimator element position value can be determined by the repetition of the steps of recording, of second establishment and second adjustment a number of times after one another, so that the in particular final second collimator element position value is determined iteratively.

Advantageously the light field, and thus the recording region for the x-ray recording can be successively made to be congruent with the marked target region in what is essentially a match without x-ray radiation falling on the patient in this case and thus a patient dose (only) being applied for adjustment purposes. The second collimator element position with the second collimator element position value can advantageously be determined very precisely and adapted especially precisely to the target region.

In accordance with one embodiment of the invention, the steps of the first and/or second determination determine the, in particular first and/or second, collimator element position value taking into account the fact that the central x-ray axis and the optical axis differ from one another. During determination the known geometrical relationship or difference between the optical axis and the central x-ray axis can be used in order to determine the collimator element position value. The distance from the x-ray source to the surface of the patient can be estimated. As an alternative first of all an average value or default value can be used as the distance. As an alternative the distance can be used via a measurement system for depth information, for example a 3D camera. Advantageously the establishment of the collimator element position value can be optimized or simplified.

In accordance with one embodiment of the invention, the distance between the examination object and the x-ray source is essentially unknown, in particular before the first and/or second determination of the second collimator element position value. Via the second collimator element position value, if necessary also via the first collimator element position value, and the size of the light field a relationship can be formed, which allows it to estimate or to determine the distance between the surface of the patient and the x-ray source.

As an alternative the use of a 3D camera, which delivers depth information, or of another depth measurement system can make it possible to adapt the first collimator element position value directly to the distance, whereby determining a second collimator element position value can be superfluous. In this embodiment of the invention, the steps showing, marking, first determination and first adjustment can be sufficient in order essentially to achieve a match between the target region and the region shown in the display. Advantageously the collimator element adjustment can be speeded up. The steps of recording, of second determination and possibly of second adjustment can be carried out for checking the first collimator element position value.

In accordance with one embodiment of the invention, the comparison comprises forming the difference between the first and second recorded optical image. Since the light field in the recorded optical image can only be seen under some conditions, the visibility of the light field can be improved by comparing images, for example by subtraction, of the changing optical images recorded one after the other on the RGB image shown on the screen. In particular the edges or the outline of the light field can be obtained via pattern recognition, for example based on a subtraction image of the optical images recorded, in particular one after the other. The distance between an edge or an outline can then be used in the second determination step in order to determine the second collimator element position value. Advantageously this method can be optimized.

In accordance with one embodiment of the invention, the comparison comprises forming a difference between the contour of the target region, in particular in the first recorded optical image or in the second recorded optical image, and the contour of the first light field, in particular in the second recorded optical image, or of the second light field.

The target region can be shown in the second recorded optical image, in particular at the same position as in the first recorded optical image. The contour can comprise an edge or a number of edges or an outline. Through the use of the contour of the target region and the contour of the first light field or of the second light field the collimator element position value in particular can be determined especially easily. The, in particular punctiform or sectional, distance between the contour of the target region and the contour of the first or second light field can advantageously be taken into account when establishing the first or second collimator element position value. In this case in particular the geometrical relationship between the optical axis and the central x-ray axis can advantageously be taken into account.

In accordance with one embodiment of the invention, the marking step comprises the following sub-steps:

Showing a geometrical object in the first recorded optical image displayed, and

Adapting the object shown by way of user signals input via a user interface to identify the target regions in the first recorded optical image displayed.

Different options can be provided for marking the region to be shown on the recorded optical image. In this way it is possible to show a geometrical object on the recorded optical image displayed, for example in the form of circles, ovals, rectangles or other forms of object, which are superimposed on the actual recorded optical image, so that the recorded optical image still remains visible however. The user can then shift the objects to the position that he wishes to designate as the target region. Likewise he can adapt the form and/or size of the objects shown via corresponding user signals, for example reduce or enlarge them or define sections of the object. Preferably the geometrical objects are shown automatically and the geometrical objects are adapted manually to the target region to be shown. After conclusion of the adaptation work by the user there is preferably provision for the user to enter a validation signal via the user interface, which is intended to signal that the adaptation process has been completed. As an alternative the validation signal is dispensed with and the user can signal this, indirectly for example, via the initiation of the radiation. Thus the data of the adapted object shown is used for computation of the position data for the collimator element. This is done by a determination unit or via a processor, to which the collimator element geometry or the geometry of the entire collimator element system is known.

An alternate marking option includes the user defining a target region by entering position data at the user interface. For example the user can click on a specific sequence of positions on the recorded optical image, through which then subsequently after detection of an end signal a polygonal shape is automatically drawn to identify the target region. In a development of the invention the polygonal shape can then subsequently still be adapted by the user, in particular in respect of form and size, in order to identify the target region in the optimum possible way. Subsequently the marking data is then used for computation of the collimator element position values. It is likewise possible to combine both of the marking variants mentioned above.

Moreover an advantageous development of at least one embodiment of the invention makes provision for an error signal to be output automatically at the user interface if impermissible marking data has been entered or acquired by the system, if for example the user has entered invalid position specifications, for example positions that lie outside the radiation region or the Field of View (FOV). If invalid marking data is acquired, then the user is usually requested to correct his marking data. If he does not meet this request or for invalid marking data either a warning can be output at the user interface that the collimator element system cannot be adjusted with the current marking data, or the continuation of the imaging examination can be aborted or interrupted.

In accordance with one embodiment of the invention, the first adjustment of the first collimator element position and/or the second adjustment of the second collimator element position is carried out automatically via a motorized computer-controlled positioning mechanism. Advantageously the first or second collimator element position value can be adjusted automatically without the user having to transmit values manually. Advantageously an especially precise positioning of the collimator element can be achieved.

At least one embodiment of the invention further relates to a collimator element adjustment unit, comprising:

A user interface, at which a first recorded optical image is displayed, in which at least one region to be shown as the target region is able to be marked, A determination unit, which is intended for automatic determination of collimator element position values, based on marking data for the target region entered via the user interface and based on geometrical parameters of the collimator element system, A computer-controlled positioning mechanism, which adjusts the collimator element system with the collimator element position values determined by the determination unit.

The user interface can involve a monitor or screen of a connected control PC, for example a control console. A light-beam localizer can be provided on which the x-ray radiation field to be shown or restricted by collimator elements on the patient to be examined is able to be displayed optically.

Displayed at the user interface is a first recorded optical image. In the first recorded optical image at least the region to be shown is able to be marked as the target region. The target region is able to be marked by a user for example. As an alternative the target region is able to be marked by a segmentation unit, in particular via the user interface. The given segmentation unit can for example receive a command, e.g. region of the body to be recorded, from the user interface and define a target region based on the first recorded optical image and mark it at the user interface displayed in the first recorded optical image. The user can adapt or correct the marked target region if required.

As an alternative, the determination unit can also be a component of the collimator element system and not be integrated directly into the collimator element adjustment unit, but in particular only be connected to it for exchange of data. In this form of embodiment of the invention the acquired marking data, which identifies the selected region, is sent to the determination unit of the collimator element system, which then automatically determines the collimator element position values from said data, in order to the adjust itself automatically. It is also conceivable to provide the determination unit in a control unit and/or in a computer/PC.

In an advantageous development, the collimator element adjustment unit additionally comprises an acquisition module. The acquisition module serves to acquire geometrical parameters and computing specifications of the collimator element system. In this case this involves in particular the type of the collimator elements used, the distances between x-ray source and x-ray detector or the collimator elements employed. Usually data in respect of the collimator element geometry is acquired automatically and in updated form in each case and forwarded to the acquisition module.

The determination unit serves to determine all required collimator element position values automatically, which are required in order to position the collimator elements of the collimator element system. As already described above, the collimator element position values comprise data in respect of the type, shape, size and position of the collimator elements used and if necessary filters.

The determination unit is preferably connected via a bus system or a network to the computer-controlled positioning mechanism, in order to be able to pass on the corresponding control commands. The positioning mechanism is then activated according to the acquired collimator element position values, in order to be able to achieve an automatic positioning of the collimator elements used and if necessary filters.

Thus an x-ray system is expanded in such a way that it comprises a determination unit, which serves to map or to establish automatically acquired marking data for a region to be shown automatically in collimator element position values. The determination unit can be implemented as a software module or as a hardware module on the control console and/or another computer-based entity. Moreover it is possible to provide the determination unit as a separate entity, which is connected via a corresponding data connection to the x-ray system or the collimator element adjustment unit and to the user interface for exchange of data.

At least one embodiment of the invention further relates to an x-ray system having an inventive collimator element adjustment unit of at least one embodiment. Preferably the imaging device is thus based on x-rays. This can involve a usual x-ray device of a computed tomography system.

The type of imaging is not defined for the application of embodiments of the invention and can be done in imaging with x-rays for example via projective recordings or tomograms. The imaging can be based on a direct-converting or indirect-converting x-ray detector, which as image converter converts the detected x-ray radiation into visible light and into an optical image able to be displayed on a screen.

Furthermore the x-ray system can be embodied to create a static recording or as continuous fluoroscopy to create a number of recordings over time, for example to display movements of the x-rayed structures or dynamic changes in a concentration of contrast medium in blood vessels or the like. Advantageously the collimator element position value can be determined automatically. Advantageously the user can control or check the region to be shown from an operating console or a user interface.

A number of advantages can be achieved with at least one embodiment of the invention. Thus, the user can operate the x-ray system significantly more quickly and more easily, since he only has to indicate one target region at the user interface or a segmentation unit carries out the marking. He no longer has to adjust the individual collimator elements in order to indicate a target region. In addition he does not have to worry about the individual collimator elements, but can concentrate exclusively on the region to be shown in the display. In the operative environment in particular this is a considerable advantage, since the adjustment process for the collimator elements can be greatly shortened and simplified.

At least one embodiment of the invention further relates to a computer program product with a computer program, which is able to be loaded directly into a memory device or a control device of an x-ray system, with program sections for carrying out all steps of at least one embodiment of an inventive method when the computer program is executed in the control device of the x-ray system.

At least one embodiment of the invention further relates to a product, in particular a computer program product, which can be loaded into an internal memory of a digital computer and comprises software routines with which the steps of at least one embodiment of the methods described above are carried out, when the software routines are loaded onto the digital computer and/or executed. In such cases the software routines can be embodied as a computer program. The computer program can be stored on a storage medium (comprising an exchangeable storage medium, such as memory cards for example). The determination unit can serve to carry out the methods described above.

At least one embodiment of the invention further relates to a computer-readable medium, on which program sections able to be read in and executed by a processor unit are stored in order to carry out all steps of at least one embodiment of an inventive method when the program sections are executed by the collimator element adjustment unit.

FIG. 1 shows an example of a schematic diagram of an embodiment of the inventive method V. The method V for collimator element adjustment of an x-ray system with a central x-ray axis and an optical axis differing therefrom of an optical imaging device comprises at least the steps of displaying V1, of marking V3, of first determination V5 and of first adjustment V7. The method V can further comprise the steps of recording V9, of second determination V11 and of second adjustment V13.

Before the first step of displaying V1, a preliminary recording V0 can be carried out, in which the first optical image is recorded, either without the light field shown or with a default light field for example. In the displaying step V1 a first recorded optical image of the examination object is displayed. In the marking step V3 a target region (ROI) is marked as the region to be shown in the first recorded optical image shown.

In the first determination step V5 at least one first collimator element position value based on the marked target region in the first recorded optical image is determined. In step V5, on the basis of the marking data and taking into account geometrical parameters of the collimator element system KS collimator element position values are determined automatically.

The geometrical parameters involve parameters of the collimator element geometry, which are usually read in via an acquisition module. The collimator element geometry parameters and the computation specifications (for application of the optical-physical projection laws) are provided automatically by the x-ray device 1 and forwarded to a determination unit or processing unit. In the first adjustment step V7 the first collimator element position is adjusted with the at least one first collimator element position value determined.

In the recording step V9, a second optical image is recorded with a first light field shown in the display with the at least one adjusted collimator element position value. In the second determination step V11 at least one second collimator element position value is determined based on the comparison of the first light field and of the target region in the second recorded optical image. In the second adjustment step V13 the second collimator element position is adjusted with the at least one second collimator element position value determined. In any repetition loop V17 the steps of recording, of second determination and of second adjustment are repeated, so that the second collimator element position value is determined iteratively. The second collimator element position value is the final collimator element position value. In step V15 the x-ray recording is carried out with the final second collimator element position. The step V15 can alternatively occur after the step V7 if the steps V9, V11 and V13 are not used.

Figure 2:
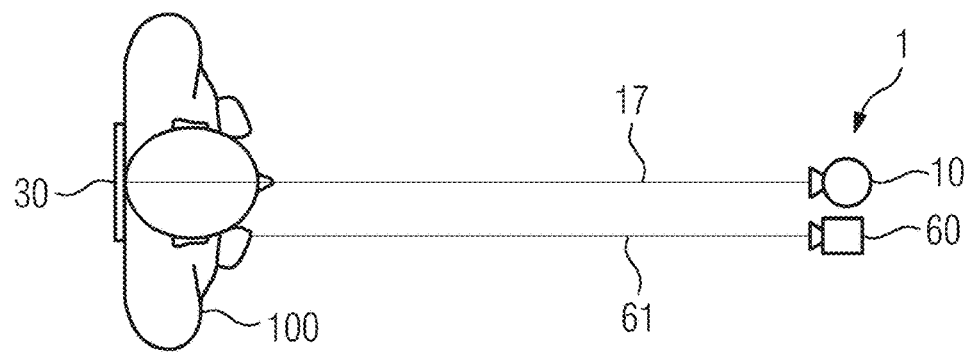
FIG. 2 shows a schematic diagram of an embodiment of an inventive x-ray system in a first form of embodiment.

FIG. 2 shows an example of a schematic diagram of an inventive x-ray system 1 in a first form of embodiment. The x-ray system 1 has central x-ray axis 17 of the x-ray source 10 and an optical axis 61 of an optical imaging device 60 differing therefrom. The x-ray source 10 and the optical imaging device 60 are arranged next to one another or adjacent. The examination object 100 is arranged between the x-ray source 10 and the x-ray detector 30. The optical axis 61 and the central x-ray axis 17 run parallel and arranged laterally offset in relation to one another. The optical axis 61 and the central x-ray axis 17 are not congruent.

Figure 3:
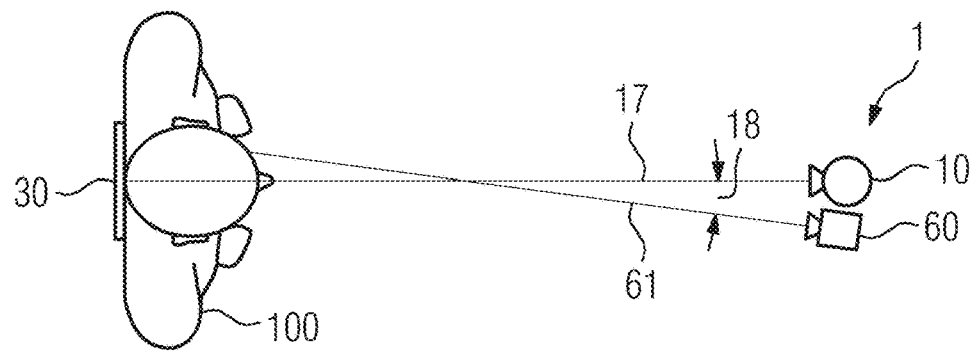
FIG. 3 shows a schematic diagram of an embodiment of an inventive x-ray system in a second form of embodiment.

FIG. 3 shows an example of a schematic diagram of an inventive x-ray system 1 in a second form of embodiment. The optical axis 61 and the central x-ray axis 17 run at an angle 18 to one another.

Figure 4:
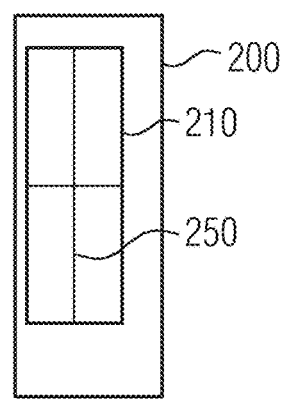
FIG. 4 shows a schematic diagram of the target region and of the first light field.

The FIG. 4 shows an example of a schematic diagram of the target region 200 and of the first light field 210. The first light field 210 is smaller than the target region 200. The first light field 210 lies within the target region 200. Shown in the first light field 210 is a crosshair 250 to indicate the central position at the intersecting point of the crosshair 250.

Figure 5:
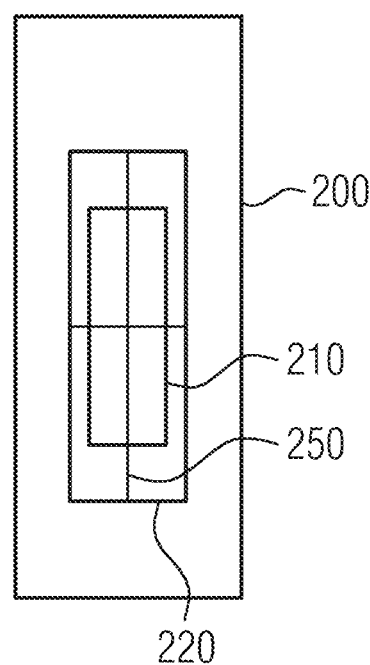
FIG. 5 shows a schematic diagram of the target region, of the first light field and of the second light field.

FIG. 5 shows an example of a schematic diagram of the target region 200, of the first light field 210 and of the second light field 220. Shown in the second light field 220 is a crosshair 250 to indicate the central position at the intersection point of the crosshair 250. The second light field 220 furthermore deviates from the target region 200, so that repetition loops are needed in order to achieve a match between the second light field 220 and the target region 200.

Figure 6:
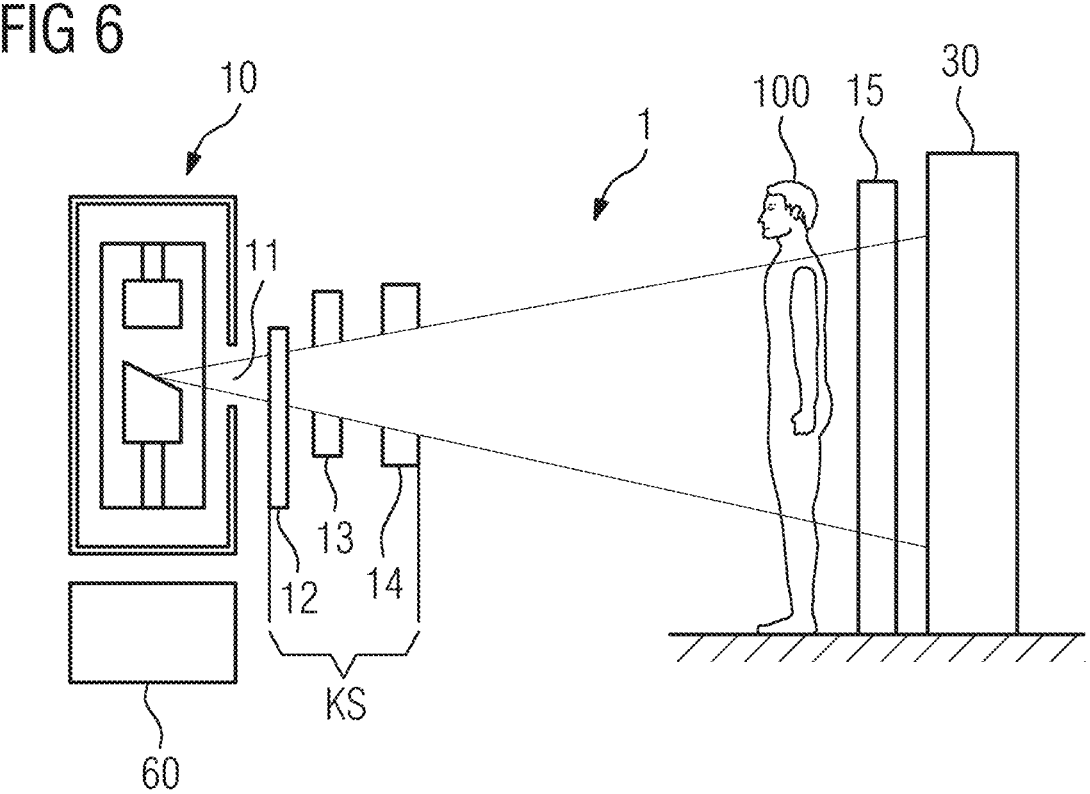
FIG. 6 shows a schematic diagram of an embodiment of an inventive x-ray system in a third form of embodiment.

FIG. 6 shows an example of a schematic diagram of an x-ray system 1 in accordance with a third form of embodiment with a collimator element system KS having a radiation filter 12, an iris collimator element 13 and a collimator element 14, in particular embodied as a lead leaf collimator element. It comprises an x-ray source 10, which is intended to emit x-rays, which are to act on the patient or a region of the patient or examination object 100 to be examined, in order subsequently to be detected by an x-ray detector 30. A scatter radiation grating 15 can also be provided between examination object 100 and x-ray detector 30. The imaging device 60 is arranged next to the x-ray source 10.

The collimator elements are preferably arranged as collimator elements 13, 14 between the x-ray source 10 and the patient 100. As an alternative the collimator element system KS can also comprise detector-side collimators (e.g. a scattered radiation grating 15). It is likewise possible for the collimator element system KS to comprise one or more ray filters 12. The collimator elements of the collimator element system KS can be of different types and comprise an iris collimator element 13 and/or a collimator element 14. The x-ray radiation of the x-ray source 10 emerging from a radiation exit window 11 can pass through different collimator elements, which can be embodied as filters 12 and/or collimator elements 13, 14, before it strikes the examination object 100.

Figure 7:
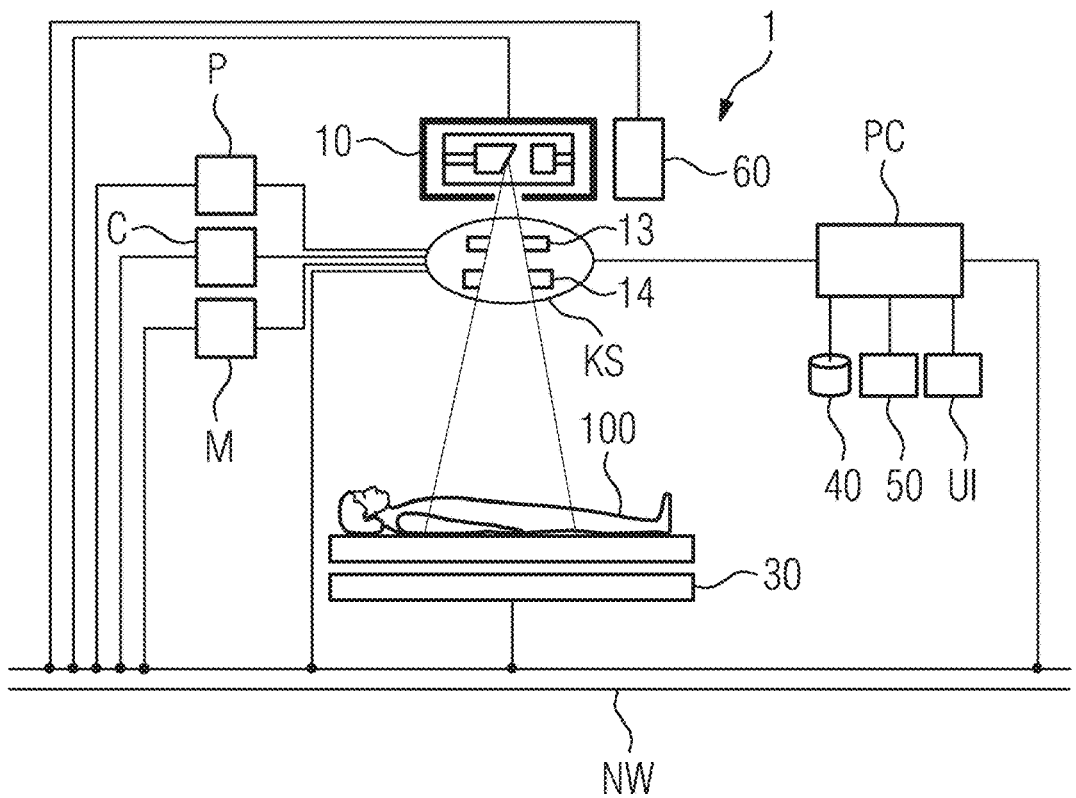
FIG. 7 shows a schematic diagram of an embodiment of an inventive x-ray system in a fourth form of embodiment.

FIG. 7 shows a schematic diagram of an inventive x-ray system in a fourth form of embodiment.

A number of units are assigned to the x-ray system. The x-ray system 1 and the collimator element system KS are controlled via a computer PC, which can be embodied as a control console. The computer PC comprises a memory 40, a keyboard 50 and a user interface UI. The x-ray system 1 moreover comprises a determination unit P that is intended for automatic computation of collimator element position values.

In alternative forms of embodiment of the invention, the determination unit P can also be embodied on other computer-based entities (e.g. on a control unit C and/or on a PC/control console). Moreover a control unit C is provided and a computer-controlled positioning mechanism M, which activates a motor in order to bring the collimator elements and/or filters of the collimator element system KS into the determined collimator element position. All of the units given above, in particular the determination unit P, the optical imaging device 60, the control unit C and the Motor M are connected to the computer PC and to the other entities of the x-ray system 1 via a network NW or a bus system or a preferably bidirectional data connection (on one side—in the direction towards the collimator elements—for exchange of position data and on the other side—in the direction from the collimator elements—of geometrical data or configuration data in relation to the collimator elements being employed in each case).

Figure 8:
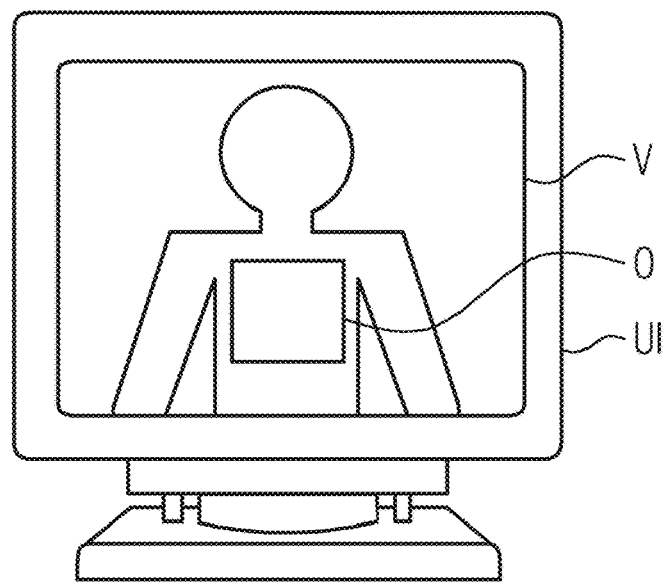
FIG. 8 shows an example of a user interface with a marking variant for marking a target region.

Shown schematically in FIG. 8 is the user interface UI, on which the first recorded optical image V is displayed showing a recording of the upper part of a human body for example. The first recorded optical image V involves a recorded optical image of the patient 100 to be examined or of the respective region of the body. The first recorded optical image V is shown on the user interface UI. The user is then given different options for marking a target region O. The target region O is then to be correctly shown in the image with the collimator elements of the collimator element system.

Although the invention has been illustrated in greater detail by the preferred example embodiment, the invention is not restricted by the disclosed examples and other variations can be derived herefrom by the person skilled in the art, without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for collimator element adjustment of an x-ray system with a central x-ray axis and an optical axis of an optical imaging device differing therefrom, the method comprising:
    displaying a first recorded optical image of an examination object;
    marking a target region as a region to be shown in the first recorded optical image displayed;
    determining at least one first collimator element position value based on the target region marked in the first recorded optical image; and
    adjusting a position of collimator element position based upon the at least one first collimator element position value determined,
    wherein the determining establishes the collimator element position value taking into account the central x-ray axis and the optical axis differing from one another, and
    wherein a distance between the examination object and the x-ray source is essentially unknown.

2. The method of claim 1, further comprising:
    recording a second recorded optical image with a first light field shown, with the at least one collimator element position value adjusted;
    subsequently determining at least one second collimator element position value based on a comparison of the first light field and a target region in the second recorded optical image; and
    subsequently adjusting the collimator element position based upon the at least one second collimator element position value determined.

3. The method of claim 2, wherein the recording, the subsequent determining and the subsequent adjusting are repeated, so that the at least one second collimator element position value is determined iteratively.

4. The method of claim 2, wherein the first light field is shown in a display in relation to the central x-ray axis.

5. The method of claim 2, wherein the first recorded optical image is recorded in relation to the optical axis.

6. A non-transitory computer program product storing a computer program, directly loadable into a memory device of a control device of an x-ray system, including program sections for carrying out the method of claim 2 when the computer program is executed in the control device of the x-ray system.

7. A non-transitory computer-readable medium, storing program sections readable and executable by a processing unit, to carry out the method of claim 2 when the program sections are executed by the processing unit.

8. The method of claim 2, wherein the comparison includes forming a difference between the first recorded optical image and the second recorded optical image.

9. The method of claim 8, wherein the comparison comprises forming a difference between a contour of the target region and a contour of the first light field.

10. The method of claim 1, wherein the at least one first collimator element position value is a central position of a light field or is a light field size.

11. The method of claim 1, wherein the first recorded optical image is recorded in relation to the optical axis.

12. The method of claim 1, wherein the marking comprises:
    showing a geometrical object in the first recorded optical image displayed; and
    adapting the object shown, via user signals entered via a user interface, to indicate the target regions in the first recorded optical image displayed.

13. The method of claim 1, wherein the adjusting of the first collimator element position is carried out automatically, via motorized computer-controlled positioning mechanism.

14. A non-transitory computer program product storing a computer program, directly loadable into a memory device of a control device of an x-ray system, including program sections for carrying out the method of claim 1 when the computer program is executed in the control device of the x-ray system.

15. A non-transitory computer-readable medium, storing program sections readable and executable by a processing unit, to carry out the method of claim 1 when the program sections are executed by the processing unit.

16. A collimator element adjustment unit for collimator element adjustment of a collimator element system with a central x-ray axis and an optical axis of an optical imaging device differing therefrom, comprising:
    a user interface, at which a first recorded optical image of an examination object is shown, at least one region of the first recorded optical image being markable as a target region to be shown in the optical image;
    a determination unit, to automatically determine collimator element position values, based on marking data for the target region entered via the user interface and based on geometrical parameters of the collimator element; and
    a computer-controlled positioning mechanism, to adjust the collimator element system with the collimator element position values determined by the determination unit,
    wherein the determination unit automatically determining collimator element position values establishes the collimator element position value, taking into account the central x-ray axis and the optical axis differing from one another, and
    wherein a distance between the examination object and an x-ray source is essentially unknown.

17. An x-ray system having the collimator element adjustment unit of claim 16.

18. A method for collimator element adjustment of an x-ray system with a central x-ray axis and an optical axis of an optical imaging device differing therefrom, the method comprising:
    displaying a first recorded optical image of an examination object;

marking a target region as a region to be shown in the first recorded optical image displayed;
determining at least one first collimator element position value based on the target region marked in the first recorded optical image;
adjusting a position of collimator element position based upon the at least one first collimator element position value determined;
recording a second recorded optical image with a first light field shown, with the at least one collimator element position value adjusted;
subsequently determining at least one second collimator element position value based on a comparison of the first light field and a target region in the second recorded optical image; and
subsequently adjusting the collimator element position based upon the at least one second collimator element position value determined,
wherein the comparison includes forming a difference between the first recorded optical image and the second recorded optical image.

19. The method of claim 18, wherein the comparison comprises forming a difference between a contour of the target region and a contour of the first light field.

20. The method of claim 18, wherein the recording, the subsequent determining and the subsequent adjusting are repeated, so that the at least one second collimator element position value is determined iteratively.

21. The method of claim 18, wherein the at least one first collimator element position value is a central position of a light field or is a light field size.

22. The method of claim 18, wherein the first recorded optical image is recorded in relation to the optical axis.

23. The method of claim 18, wherein the first light field is shown in a display in relation to the central x-ray axis.

24. The method of claim 18, wherein determining establishes the collimator element position value taking into account the central x-ray axis and the optical axis differing from one another.

25. The method of claim 18, wherein the determining establishes the collimator element position value taking into account the central x-ray axis and the optical axis differing from one another.

26. The method of claim 18, wherein a distance between the examination object and the x-ray source is essentially unknown.

27. The method of claim 18, wherein the marking comprises:
showing a geometrical object in the first recorded optical image displayed; and
adapting the object shown, via user signals entered via a user interface, to indicate the target regions in the first recorded optical image displayed.

28. The method of claim 18, wherein the adjusting of the first collimator element position is carried out automatically, via motorized computer-controlled positioning mechanism.

29. A non-transitory computer program product storing a computer program, directly loadable into a memory device of a control device of an x-ray system, including program sections for carrying out the method of claim 18 when the computer program is executed in the control device of the x-ray system.

30. A non-transitory computer-readable medium, storing program sections readable and executable by a processing unit, to carry out the method of claim 18 when the program sections are executed by the processing unit.

* * * * *